United States Patent [19]

Weeks

[11] 4,032,406
[45] June 28, 1977

[54] DOPAMINE-β-HYDROXYLASE DETERMINATION METHOD

[75] Inventor: Lloyd E. Weeks, St. Louis, Mo.

[73] Assignee: Monsanto Company, St. Louis, Mo.

[22] Filed: Dec. 4, 1975

[21] Appl. No.: 637,805

[52] U.S. Cl. .................................. 195/103.5 R
[51] Int. Cl.² .................................. G01N 31/14
[58] Field of Search .......... 195/103.5 R; 204/195 P

[56] References Cited

UNITED STATES PATENTS 3,838,011  9/1974  Hagen et al. ............... 195/103.5 C
3,857,771  12/1974  Sternberg ................... 195/103.5 R

OTHER PUBLICATIONS

Nagatsu et al., "Photometric Assay of Dopamine-β-Hydroxylase Activity in Human Blood", Clin. Chem., vol. 18, No. 9 (1972) pp. 980–983.
Goldstein et al., "Kinetic Studies of the Enzymatic Dopamine β-Hydroxylation Reaction", Biochemistry, vol. 7, No. 8 (1968) pp. 2724–2730.
Kadish et al., "A New and Rapid Method for the Determination of Glucose by Measurement of Rate of Oxygen Comsumption", Clin. Chem., 14–2 (1968), pp. 116–131.
Sweetman et al., "The Oxidation of Biologically Important Monamines by Monamine Oxidase", Exp. in Physiol. & Biochem. (1972) 5, pp. 303–328.

Primary Examiner—Lionel M. Shapiro
Assistant Examiner—C. A. Fan
Attorney, Agent, or Firm—John D. Upham; Scott J. Meyer

[57] ABSTRACT

A method of determining dopamine-β-hydroxylase (DβH) activity in biological fluids which comprises reacting a DβH-specific substrate with a sample of said biological fluid in the presence of ascorbate, fumarate and oxygen and measuring the uptake of oxygen by the resulting hydroxylation with an oxygen-sensing electrode.

6 Claims, No Drawings

DOPAMINE-β-HYDROXYLASE DETERMINATION METHOD

BACKGROUND OF THE INVENTION

This invention relates to a method for the determination of dopamine -β- hydroxylase, hereinafter referred to as DβH. More particularly, this invention relates to a method for the determination of DβH activity in biological fluids with an oxygen-sensing electrode which measures dissolved oxygen in solution.

DβH is an enzyme which catalyzes the oxidation of dopamine to norepinephrine according to the following equation:

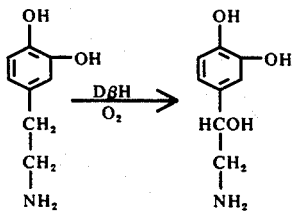

Dopamine, which is one of the biogenic amines, has been shown to play an important role in the sympathetic motor system. A diminished supply of dopamine in the corpus striatum of the brain is associated with Parkinson's disease. The enzyme DβH, which oxidizes the catecholamine dopamine to norepinephrine, is apparently released from the sympathetic nerves together with the catecholamines. An elevated level of DβH has been associated with hypertension and it has been proposed that plasma DβH activity may serve as an index of the activity of the sympathetic nervous system, Schanberg et al, Science 183, 523-4 (1974). Consequently, methods for the determination of DβH are of significant clinical interest.

Presently available methods for the determination of DβH in biological fluids include a fluorometric method which employs dopamine as the substrate, Von Euler et al, *Acta Physiol. Scand.* 33, 45 (1955); an enzyme conversion method employing tyramine-³H as the substrate based on the conversion of tyramine to octopamine and oxidation of the latter compound with periodate, Pisano et al, *Biochim.Biophys. Acta* 43, 566 (1960); a non-isotopic method employing similar such conversion of tyramine, Kuzuya and Nagatsu, *Enzymologia* 36, 31 (1969); and a photometric procedure involving the photometric assay of p-hydroxybenzaldehyde following the previously described oxidation of the octopamine with periodate, Nagatsu and Udenfriend, *Clin. Chem.* 18, 980-83 (1972).

Although the foregoing assay procedures are useful and sensitive, they involve numerous steps and are time consuming.

SUMMARY OF THE INVENTION

In accordance with the present invention, a method is provided for the rapid determination of DβH with an oxygen-sensing electrode system. The method involves the enzymatic conversion of a DβH-specific substrate by DβH to the corresponding β-hydroxylated compound in which an oxygen-sensing electrode is used to determine the uptake of dissolved oxygen by the hydroxylation reaction. The rate of change in the electrode output is proportional to the activity of DβH. This method advantageously requires fewer steps than prior methods and can be conveniently carried out within several minutes as opposed to the several hour time required carried for the photometric assay method.

DETAILED DESCRIPTION OF THE INVENTION

In general, the method of the present invention involves hydroxylation of the DβH-specific substrate in the presence of a suitable reagent system which is catalyzed by the DβH present in the biological fluid to be analyzed. The dissolved oxygen consumed by the hydroxylation reaction is then measured by an oxygen-sensing electrode. The reagent system used in this hydroxylation reaction comprises an aqueous medium containing substances that facilitate the reaction.

The DβH-specific substrate generally employed in this invention is an aromatic alkyl amine which DβH is able to convert to the corresponding β-hydroxylated amine, particularly phenylethylamine, phenylpropylamine and their derivatives. Of these amine substrates, the primary phenylethylamines and phenylpropylamines are preferred over the corresponding secondary amines; the phenylethylamines are preferred over the phenylpropylamines; and the p-hydroxy and 3,4-dihydroxy ring substituted amines are preferred over the corresponding unsubstituted amines. Examples of these amine-substrates and the corresponding β-hydroxylated amines are the following:

| Substrate | Product |
| --- | --- |
| phenylethylamine | β-phenylethanolamine |
| phenylpropylamine | β-phenylpropanolamine |
| p-hydroxyphenylethylamine | p-hydroxyphenylethanolamine |
| p-hydroxyphenylpropylamine | p-hydroxyphenylpropanolamine |
| 3,4-dihydroxyphenylethylamine | 3,4-dihydroxyphenylethanolamine |
| 3,4-dihydroxyphenylpropylamine | 3,4-dihydroxyphenylpropanolamine |
| 3,4-dihydroxyphenylethyl-methylamine | 3,4-dihydroxyphenyl-2-methylaminoethanol |
| 1-phenyl-2-aminopropane | 2-amino-1-phenyl-1-propanol |
| α-methyl-dopamine | nordefrin |
| p-hydroxyamphetamine | p-hydroxynorephedrine |
| α-methyl-m-tyramine | m-hydroxynorephedrine |

The board specificity of the enzyme DβH to catalyze the β-hydroxylation of a wide variety of aromatic alkyl amines such as the foregoing is disclosed by Goldstein, *J. Biol. Chem.* 237, 1898–1902 (1962) and Van der Schoot and Creveling, in "Advances in Drug Research," edited by Harper and Simmonds, Academic Press, New York, pp. 47–88 (1965), said disclosures being incorporated herein by reference.

The most preferred substrates for use in the present invention are p-hydroxyphenylethylamine (tyramine) and 3,4-dihydroxyphenylethylamine (dopamine). Although the present invention is further described in detail using tyramine and dopamine as the illustrative substrates, it should be understood that other DβH-specific substrates, including those exemplified above, can also be used in the invention.

The particular reagent system used for carrying out the hydroxylation reaction is based on the nature of the DβH enzyme. Thus, certain substances, such as ascorbate and fumarate, are believed to be essential cofactors which stimulate the enzyme reaction and, therefore, are included in the reagent system. The method of the invention thereby employs the following general reaction, using tyramine as the illustrative substrate:

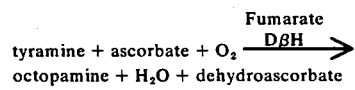

$$\text{tyramine} + \text{ascorbate} + O_2 \xrightarrow[\text{DβH}]{\text{Fumarate}} \text{octopamine} + H_2O + \text{dehydroascorbate}$$

The DβH enzyme is known to be a copper protein and it has been shown to undergo cyclic reduction and oxidation during the overall hydroxylation reaction. The reagent system thus contains the above-mentioned ascorbate whereby the cupric copper of the enzyme is reduced by the ascorbate and partially reoxidized when the reduced enzyme reacts with the amine substrate and oxygen.

The above-described fumarate, which is known to stimulate the hydroxylation reaction, is included in the reagent system for such purpose although its specific mechanism is obscure.

Other substances which can be employed in the reagent system are acetate, catalase, N-ethylmaleimide, and pargyline. Acetate is a known stimulant of the hydroxylation reaction, while catalase, N-ethylmaleimide and pargyline are used for various inhibitory purposes. Thus, catalase is preferably used in the reagent system to protect the DβH enzyme from the $H_2O_2$ which is formed by the nonenzymatic oxidation of ascorbic acid, and N-ethylmaleimide is used to protect the DβH from endogenous inhibitors in the biological fluid being analyzed.

Another component preferably included in the reagent system is the above-mentioned pargyline, which is a monoamine oxidase inhibitor. When used, pargyline preferably is incorporated in the reagent system as a water soluble salt such as, for example, the hydrochloride.

The amine, fumarate and acetate components also preferably are employed in the form of their water soluble salts such as, for example, the amine hydrochloride and the fumarate and acetate sodium salts.

The specific amounts of the foregoing substances used in the reagent system are not critical to the invention and can be readily determined by the person skilled in the art without undue experimentation by reference to the specific examples set forth hereinafter. Further information on the use of these substances in reagents for the determination of DβH can also be had by reference to Nagatsu and Udenfriend, *Clin. Chem.* 18, 980–83 (1972); Goldstein et al, *Biochemistry* 7, 2724–30 (1968); and references cited therein; all for the foregoing being incorporated herein by reference. In general, use of about molar equivalent amounts of the amine, ascorbate and fumarate component are suitable.

In carrying out the method of the present invention, the reagent system is admixed with DβH-specific substrate in suitable proportions in a cuvette or other such sample container with an attached oxygen-sensing electrode. An attached recorder for the electrode which indicates the electrode output is allowed to equilibrate. Then a suitable amount of a sample of the biological fluid to be analyzed for the presence of DβH, such as blood or plasma, is admixed with the reagent system/substrate mixture, and the rate of change in the electrode output resulting from the oxygen consumption by the hydroxylation of the DβH-specific substrate is measured. The required oxygen for the reaction can be conveniently provided by saturating the reagent solution with air or oxygen.

The proportions of substrate, reagent system solution and the biological sample can vary widely and are adjusted to convenient levels based on laboratory needs and the expected range of DβH activity in the biological samples to be analyzed.

Incubation time and temperature conditions are not critical and can be varied to facilitate completion of the reaction. Usually, the reaction is complete within about 2 to 3 minutes at incubation temperatures ranging from about 25° to 40° C.

In general, the oxygen-sensing electrode comprises an anode, a cathode, an electrolyte solution, and means whereby the diffusion flow of oxygen through a semipermeable membrane into the electrolyte is measured. The current input is a linear function of oxygen tension which in turn varies directly with the diffusion flow of oxygen.

Oxygen-sensing electrodes are well-known. The Clark $pO_2$ electrode described in U.S. Pat. No. 2,913,386 is typical. In this electrode, oxygen diffuses through a gas-permeable polymeric membrane and is reduced at a platinum cathode which is kept at a fixed potential with respect to a silver-silver chloride reference anode. Such electrodes have been used heretofore for the determination of blood glucose levels by measuring the oxygen uptake in a glucose oxidase enzyme catalyzed reaction. Illustrative of such use of the Clark $pO_2$ electrode are the report by Kunz and Stastny, *Clin. Chem.* 20, 1018–22 (1974) and the review article by Gough and Andrade, *Science* 180, 380–84 (1973). The use of oxygen-sensing electrodes for measuring monoamine oxidase enzyme activity has been described heretofore by Sweetman and Weetman, *Exp. Physiol. Biochem.* 1972, 5, pp 303–28.

Oxygen-sensing electrodes also are commercially available or can be prepared in the laboratory. One such suitable electrode, commercially available from Beckman Instruments, Inc., consists of a gold cathode which is separated by an epoxy coating from a tubular silver anode. An inner sensor body is housed in a plastic casing and comes into contact with the sample reagent solution only through a Teflon (duPont polytetrafluoroethylene) plastic membrane. As oxygen diffuses through this membrane, it is electrochemically reduced at the cathode by an applied potential of 0.8 volts. The reaction causes a current to flow between the anode and cathode which is proportional to the partial pressure of oxygen in the reagent sample.

An example of a suitable laboratory prepared oxygen-sensing electrode for measuring dissolved oxygen in solution is described by Johnson et al, *Biotechnol. J Bioeng.* 6, 457–68 (1964). This electrode has a silver cathode, a lead anode, an acetate buffer as an electrolyte, and a Teflon plastic membrane. The electrolyte is an aqueous solution containing 0.1 molar sodium acetate and 0.1 molar acetic acid, or a more concentrated solution containing 5 M acetic acid and 0.5 M sodium acetate. A modification of this electrode is described by Borkowski and Johnson, Biotechnol. J Bioeng. 9, 635–39 (1967), in which the electrolyte is an aqueous solution of 5 M acetic acid, 0.5 M sodium, 0.1 M lead acetate and has a pH of about 3. In addition, a silicone rubber insulated filter of glass wool or nylon is inserted between the lead anode and silver cathode to prevent lead particles from dropping onto the silver cathode and eventually causing a short circuit. The electrode has a linear response from below 0.00002 to over 0.2 atmosphere of oxygen. In this electrode, the reaction at the silver cathode is believed to be $$\tfrac{1}{2} O_2 + H_2O \text{ to } + 2e^- \rightarrow 2OH^-$$

while at the lead anode the loss of electrons produces lead ions.

$$Pb \rightarrow Pb^{++} + 2e^-$$

The lead ions combine with hydroxyl to form lead hydroxide on the anode surface to result in an overall reaction as follows:

$$\tfrac{1}{2} O_2 + Pb \text{ to } + H_2O \rightarrow Pb(OH)_2$$

With acetate as the electrolyte, a deposit of basic lead acetate builds up on the lead surface and lead salts accumulate in the electrolyte. The expendable materials thereby are the lead anode and the acetate of the electrolyte.

A further modification of the above-described Johnson electrode is disclosed by Elsworth, The Chemical Engineer, February 1972, pp. 63–71.

Still other oxygen-sensing electrodes for use in the present invention are described in U.S. Pat. Nos. 3,449,231, 3,454,485 and 3,539,455.

Although Teflon plastic and silicone rubber have been specifically described above, it should be understood that other membrane materials permeable to oxygen and impermeable to water and electrolytes can be used in the oxygen-sensing electrode, for example, polyethylene, polypropylene, polystyrene and polyvinyl chloride. Other suitable anode-cathode materials, include, for example, any noble metal cathode such as gold, silver or rhodium in conjunction with a zinc, cadmium or lead anode.

In the instant invention, the flow of oxygen by diffusion through the plastic membrane is reduced by the presence of the D$\beta$H enzyme in the enzyme catalyzed reaction as defined hereinbefore. The output current of the electrode is measured after allowing sufficient time for this reaction to achieve a steady state, which generally occurs in a time interval of about 30 seconds to three minutes.

The following detailed examples will further illustrate the invention although it should be understood that the invention is not limited to these specific examples.

EXAMPLE 1

A reagent system for the determination of D$\beta$H was prepared by admixing the following components in the stated amounts:

| Component | Amount |
| --- | --- |
| Sodium Acetate, 1.0M, pH 5.0 | 6.0 ml. |
| Ascorbic Acid, 0.2M | 1.5 ml. |
| Sodium Fumarate, 0.2M | 1.5 ml. |
| Pargyline . HCl, 0.02M | 1.5 ml. |
| N-ethylmaleimide, 0.2M | 4.5 ml. |
| Catalase, 400 I.U./ml. | 3.0 ml. |
| Water, distilled | 6.0 ml. |
| Total | 24.0 ml. |

The above-prepared reagent system was saturated with air at 37° C and then a one ml. aliquot of the reagent mixture, 0.1 ml. of distilled water and 0.1 ml. of 0.2M tyramine . HCl solution were admixed in a curvette with an attached oxygen-sensing electrode.

The oxygen-sensing electrode employed in this example was a modification of the membrane electrode described by Elsworth, The Chemical Engineer, February 1972, pp. 63–71. This modification employed a silver cathode and a lead anode. The electrolyte, which consisted of 5.0M acetic acid, 0.5M sodium acetate and 0.1M lead acetate, instead of being used in a liquid phase as described by Elsworth, was employed in a gelled form by the addition of a small amount of Syton (Monsanto silica gel) and then applied in film form covered by a Teflon plastic film.

The electrode was attached to a cuvette, which had an inner Teflon plastic sleeve lining, by entry from the side of the curvette. The reagents were introduced into the cuvette by entry from the open top. An agitated water bath assembly was employed to maintain a stirring speed of about 150–400 rpm, preferably about 250 rpm, and a temperature of about 37° C for the reaction components.

A Beckman recorder attached to the electrode terminals and indicating the electrode output was allowed to equilibrate. Then 0.1 ml. of a control standard having no D$\beta$H activity (Stattrol, a commercially available serum from Worthington Biochemical Corp.) was added to the cuvette to establish a base line for the oxygen electrode determination of D$\beta$H.

Serum samples from four normal human donors were then assayed with the foregoing oxygen electrode system and the assays were compared with assays made on other portions of the same donor samples by the photometric method of Nagatsu and Udenfriend, supra, employing absorbance at 330 nm. In each of these assays, 0.1 ml. of the serum sample was used in place of the 0.1 ml. control sample previously used for equilibration. The assay results are set forth below:

| Donor Sample | Oxygen Electrode Assay* −mv/min. | Photometric Assay** Enzyme Activity |
| --- | --- | --- |
| Control | 0 | 0 |
| A | 0.55 | 18.6 |
| B | 0.66 | 22.2 |
| C | 0.68 | 10.5 |
| D | 0.70 | 7.6 |

*The rate of decrease in millivolts per minute output from the oxygen-sensing electrode.
**$\mu$ mol octopamine/minute per liter of serum.

The above results show a qualitative indication for the presence of D$\beta$H activity within the expected range of normal human sera. Human sera having an elevated level of D$\beta$H will produce assay values relatively higher than those shown, above, for normal sera.

EXAMPLE 2

The procedure of Example 1 is repeated except that dopamine.HCl is substituted for an equivalent amount of tyramine.HCl with substantially similar results.

A principal advantage of the present method of determining DβH activity is that it is carried out within about 2 to 3 minutes in a single step whereas, by comparison, the above-used multi-step photometric assay requires about 3 to 4 hours for completion.

Various other examples will be apparent to the person skilled in the art after reading the foregoing specification and the appended claims without departing from the spirit and scope of the invention. All such further examples are included within the scope of the appended claims.

What is claimed is:

1. The method of determining dopamine-β-hydroxylase (DβH) activity in blood serum or plasma comprising reacting a sample of said blood serum or plasma with a DβH-specific substrate selected from the group consisting of dopamine and tyramine in the presence of a reaction medium saturated with air or oxygen and comprising ascorbate and fumarate and measuring the uptake of said oxygen with an oxygen-sensing electrode.

2. The method of claim 1 in which the reaction medium additionally contains acetate.

3. The method of claim 1 in which the reaction medium additionally contains catalase, N-ethylmaleimide and pargyline anti-inhibitors of the reaction.

4. The method of claim 1 in which the reaction is carried out at a temperature ranging from about 25° to 40° C.

5. The method of claim 1 in which the DβH-specific substrate is tyramine, the reaction medium additionally contains acetate, catalase, N-ethylmaleimide and pargyline, and the reaction is carried out at a temperature ranging from about 25° to 40° C.

6. The method of claim 1 in which the DβH-specific substrate is dopamine, the reaction medium additionally contains acetate, catalase, N-ethylmaleimide and pargyline, and the reaction is carried out at a temperature ranging from about 25° to 40° C.

* * * * *